United States Patent [19]

Rieger

[11] Patent Number: 4,609,677

[45] Date of Patent: Sep. 2, 1986

[54] NON-STEROIDAL ANTI-INFLAMMATORY COMPOUNDS AND COMPOSITIONS THEREOF

[75] Inventor: Martin M. Rieger, Morris Plains, N.J.

[73] Assignee: Warner-Lambert Company, Morris Plains, N.J.

[21] Appl. No.: 796,033

[22] Filed: Nov. 7, 1985

Related U.S. Application Data

[63] Continuation of Ser. No. 738,920, May 29, 1985.

[51] Int. Cl.[4] .................... A61K 31/12; A61K 31/015
[52] U.S. Cl. ..................................... 514/679; 514/765
[58] Field of Search ................................. 514/679, 765

[56] References Cited

PUBLICATIONS

Chem. Abst. 97-155849k (1982).

*Primary Examiner*—Stanley J. Friedman
*Attorney, Agent, or Firm*—Howard Olevsky; Gary M. Nath

[57] ABSTRACT

A non-steroidal anti-inflammatory composition comprising a therapeutically effective amount of active anti-inflammatory agent selected from the group consisting of 1-phenyl-1 cyclohexene, 4-phenylcyclohexanone, and mixtures thereof. The active agent may be formulated in a pharmaceutically acceptable carrier. These compositions are useful in the treatment in mammals of inflammation and other related symptoms, including pain.

5 Claims, No Drawings

NON-STEROIDAL ANTI-INFLAMMATORY COMPOUNDS AND COMPOSITIONS THEREOF

This is a continuation of co-pending application Ser. No. 738,920, filed on May 29, 1985.

The present invention relates to non-steroidal anti-inflammatory compounds useful as active agents in the treatment, in mammals, of inflammation and its related symptoms, including pain; pharmaceutically acceptable compositions containing these agents; and methods of treatment employing these agents.

Non-steroidal anti-inflammatory compounds are well-known in the art. Examples of such compounds include aspirin, indomethacin, and phenylbutazone, to name a few. These compounds are known to cause side-effects, e.g., gastroenteric disorders and headaches.

U.S. Pat. No. 4,145,444 to Hamazaki et al., discloses various non-carboxylic benzoyl derivatives as anti-inflammatory agents. In particular, the compounds disclosed have the formula

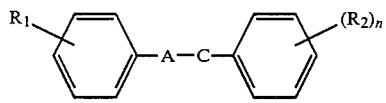

wherein $R_1$ represents hydrogen, halogen, hydroxy, $C_{1-8}$ alkyl or $C_{1-8}$ alkoxy; $R_2$ represents hydrogen, halogen, hydroxy, vinyl, $C_{1-8}$ alkyl or $C_{1-8}$ alkoxy; A represents carbonyl, methylene or a single bond; and n is an integer from 1 to 4. It is preferred that $R_2$ be $C_{3-8}$ alkyl or $C_{1-8}$ alkoxy substituted in the para position; n be 1; $R_1$ be hydrogen or halogen substituted in the ortho position; and A, a single bond, e.g., 4-n-butylbenzophenone or 4-n-butyl-2'-fluorobenzophenone.

U.S. Pat. No. 4,244,970 to Dewhirst discloses a method of treating inflammation and inhibiting prostaglandin synthesis by administering an effective amount of 2-hydroxybenzophenone and certain substituted 2-hydroxybenzophenones.

The association between the production of prostaglandins in mammals and inflammation and related symptoms is well documented. For purposes of this application, the reference to inflammation shall be read to include reference to its related symptoms including pain. See Greaves and Sondergaard, Journal of Investigative Dermatology 54:365-367, 1970, where prostaglandin activity in tissue fluid taken from inflamed human skin was first reported. Other investigators have subsequently reported that $PGE_2$ (prostaglandin $E_2$) concentrations in skin increase after exposure to ultraviolet light and mediate a significant degree of redness particularly in the first 24 hours subsequent to exposure. The literature reveals that known non-steroidal antiinflammatory agents, e.g., indomethacin, reduce ultraviolet-induced erythema by inhibiting the production of prostaglandin $E_2$ within the first 24 hour period subsequent to UVB exposure. See "Prostaglandins in the Skin," by Neal S. Penneys, published by Upjohn Co., 1980.

Without wishing to be bound by any one theory, it is believed that the inventive compositions of this application are effective prostaglandin synthesis inhibitors. It is theorized that the effective inhibition of prostaglandin synthesis is the mechanism by which the novel compounds reduce and control inflammation in mammals.

It is apparent that there is a need for effective, non-steroidal anti-inflammatory compounds which can be formulated into compositions using pharmaceutically acceptable carriers for topical, oral, rectal, sublingual or parenteral administration. The compounds of this invention fulfill this need.

The instant invention relates particularly to anti-inflammatory compositions containing a therapeutically effective amount of a compound having one of the following structural formulae:

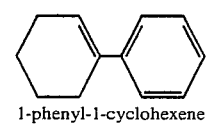

1-phenyl-1-cyclohexene

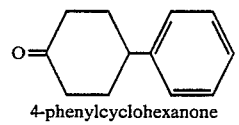

4-phenylcyclohexanone and mixtures thereof. These compounds, not previously disclosed as having anti-inflammatory properties, have been found, when administered to mammals in therapeutically effective amounts, either alone or in a pharmaceutically acceptable carrier, to be effective against inflammation. They are intended for use in the treatment of a variety of inflammatory problems and diseases including systemic diseases such as arthritis and the like.

When contained in a pharmaceutically acceptable carrier or composition, the compounds described above or mixtures thereof, (henceforth referred to as the "agent" in the composition), are generally present in therapeutically effective amounts of about 0.05% to about 25% by weight of the composition; preferably in amounts of about 0.05% to about 15% and most preferably about 0.1% to about 3% by weight of the composition.

The inventive compounds are preferably used in compositions which can be easily and conveniently administered to a mammal experiencing inflammation. Pharmaceutically acceptable carriers may be varied to produce topical creams, pastes, ointments, gels, lotions and the like, for direct application to the inflamed area; capsules, tablets, solutions, syrups, powders and the like for oral administration; and compositions appropriate for rectal, sublingual and parenteral administration.

The preferred form of composition is a topical lotion. Useful pharmaceutically acceptable carriers for this embodiment include dimethyl sulfoxide; mono- and di-alcohols and polyols including lower alkyl alcohols such as ethanol, 1,2-propylene glycol, polyethylene glycol, and glycerol; mineral oils; vegetable oils; petrolatum; nonionic, cationic, and anionic surfactants; water and the like, as well as mixtures of these. Compositions comprising such carriers and the agent in amounts of from about 0.05% to about 25% by weight of the composition have been found particularly effective in the treatment of inflammation of the skin, commonly known in the art as erythema.

The active anti-inflammatory compounds of the instant invention can be applied together with other anti-inflammatory agents, analgesics, thrombus dissolving agents, thrombus inhibiting agents, antibiotics and the like.

In the case where the anti-inflammatory agent is incorporated in a pharmaceutically acceptable composition, other common materials such as occlusives, emulsifiers, emollients, humectants, surfactants, lubricants, preservatives, waxes, thickeners, demulcents, perfumes, coloring additives and the like may be added. These, of course, are not critical to the invention and their amounts, which can be varied and balanced to meet the desired properties of the overall composition, may be determined by routine experimentation by one skilled in the art.

The instant compositions may include materials that serve as occlusives in that they hold moisture against the surface of the skin. Suitable occlusive compounds include cetyl alcohol, cetyl palmitate, petrolatum, mineral oil and the like. These materials are generally present in topical compositions, for example, in amounts of about 1% to about 25% by weight of the composition and preferably in amounts of about 2% to about 10%.

A variety of materials may be utilized as emulsifiers, including high molecular weight polyethylene glycols, fatty alcohols such as stearyl alcohol and myristyl alcohol and the like. These materials are generally present in amounts of about 0.1% to about 15% by weight of the composition and preferably in amounts of about 1% to about 10%.

Suitable emollients for use in the instant compositions containing the novel anti-inflammatory compounds include fatty acid esters such as cetyl palmitate, diisopropyl adipate, isopropyl isostearate, isostearyl isostearate and mixtures thereof, to name a few. Generally they are present in topical compositions in amounts of about 0.1% to about 20% by weight of the composition and preferably in amounts of about 1% to about 10%.

Suitable humectants may be any of those well known in the art. Examples of useful humectants include glycerin, propylene glycol, polyethylene glycol, polyhydric alcohols and mixtures thereof, to name a few. Preferably, glycerin is used. These materials may be incorporated in the inventive anti-inflammatory compositions in amounts of about 0.1% to about 30% by weight of the composition and preferably in amounts of about 3% to about 20%.

Numerous surfactants, and preferably non-ionic surfactants, may be added for their intended purpose. Among those preferred are polyalkanolamines such as triethanolamine, polyethylene glycol stearate, polyethylene glycol laurate, polyoxyethylene and polyoxypropylene compounds, e.g. derivatives of sorbitan and fatty alcohol esters, fatty acid esters of polyhydric alcohols and amine oxides; anionic surfactants, such as alkyl carboxylates, acyl lactylates, sulfuric acid esters (e.g. sodium lauryl sulfate), ester-linked sulfonates, and phosphated ethoxylated alcohols; cationic surfactants, such as monoalkyl and dialkyl quaternary ammonium salts, amidoamides and aminimides. These various surfactants, when compatible, can be added as mixtures to the instant compositions and are generally present in amounts of about 0.1% to about 15% by weight of the composition.

Lubricating agents may be used when desired in the instant compositions. They include silicone oils or fluids such as substituted and unsubstituted polysiloxanes, e.g. dimethyl polysiloxane, also known as dimethicone, is particularly useful when the composition is to be used as a topical preparation. The lubricating agents, when incorporated in a topical composition, are generally present in amounts of about 0.1% to about 30% by weight of the composition and preferably in amounts of about 1% to about 10%. Other lubricating agents well known to the tableting and capsule art may be used when the composition takes the form of a tablet, pill or capsule. These lubricating agents are used primarily to aid in formation of tablets.

Preservatives such as alkyl and aryl parabens and substituted phenols are also useful additives. Examples of the preferred parabens are the methyl, propyl and butyl parabens which may be employed in amounts of 0.1% to about 0.25% by weight of the composition. In a preferred embodiment, a combination of methyl, propyl and butyl paraben may be used in the respective amounts of about 0.1% to about 0.25%, 0.02% to about 0.2%, and 0 to about 0.05%. Examples of suitable substituted phenols include chloro-substituted phenoxy phenols, such as 5-chloro-2-(2,4-dichlorophenoxy)-phenol, hexachlorophene, triclosan and dichlorophene, among others.

Other useful preservatives include mercury derivatives, such as phenylmercuric acetate; quaternaries, such as benzethonium chloride, benzalkonium chlorides and cetyl trimethyl ammonium bromide; organic acids, such as sorbic acid; and a variety of other preservatives such as Kathon CG, a trademark of Rohm & Haas Co. which comprises a mixture of 5-chloro-2-methyl-4isothiazolin-3-one and 2-methyl-4-isothiazolin-3-one.

In addition, conventional additives such as waxes, thickeners, demulcents, fragrance oils, color additives, and other materials may be included. For example, in the case of a topical lotion, thickeners for viscosity adjustment would include xanthan gum, sodium stearyl sulfate, and materials of that type.

The foregoing recitation of materials is presented for purposes of illustration and not limitation, it being understood that a variety of equivalent materials would all function in the capacities set forth above.

The instant invention also includes a method of treatment for inflammation whereby a mammal is administered a therapeutically effective amount of 1-phenyl-1-cyclohexene, 4-phenylcyclohexanone, or mixtures thereof.

It should be recognized that the process for preparing the anti-inflammatory compositions of this invention which employ a pharmaceutically acceptable carrier are considered well known and not a part of this invention. Such routine procedures involving blending, molding, tableting and so forth are well within the scope of the ordinary artisan.

The invention will be further appreciated by the following example which illustrates two embodiments of the instant invention. All percentages throughout the specification and claims are by weight of the total composition unless otherwise indicated.

EXAMPLE

This example is designed after the guinea pig model of Snyder, Journal of Investigative Dermatology, 64: 322-25, 1975, and demonstrates that skin inflamed by ultraviolet light (U.V.B.) can be therapeutically treated using compounds of the instant invention. Since it is known that U.V.B. irradiation-induced erythema is prostaglandin mediated, this example additionally demonstrates that the instant compounds when applied topically in a dermatological preparation are effective in inhibiting the production of prostaglandins.

The dorsal surface of a male albino guinea pig was shaved with a standard animal clipper (#40 head), depilated with a commercially available thioglycolate based depilatory product, rinsed with tap water and dried. The animal was immobilized in a standard head stock and irradiated for 30 minutes under a bank of Westinghouse FS-40 lamps. This period of irradiation was found to be equivalent to 3 MED's. An MED (minimum erythemal dose) is the minimum amount of U.V.B. radiation required to produce sunburn 24 hours subsequent to exposure.

Immediately after irradiation, the animal's exposed dorsal surface was delineated with a black marking pen into treatment sites. Different sites were treated with ten (10) micro-liters of (A) a 3% by weight solution of 1-phenyl-1-cyclohexane in 90% dimethyl sulfoxide (DMSO) (Compound A), (B) a 3% by weight solution of 4-phenylcyclohexanone in 90% DMSO (Compound B), and (C) a 3% by weight solution of 2-hydroxy-4-methoxybenzophenone in 90% DMSO as a control, this benzophenone compound being disclosed in U.S. Pat. No. 4,244,970 of Dewhirst. The sites were then visually evaluated for lack of erythema (blanching) at 1, 5 and 24 hours post-treatment. The results, as described below, were based on the following scale:

0—No Blanching
1—Barely Detectable Blanching
2—Moderate Blanching
3—Severe Blanching
4—Complete Blanching (no erythema).

The results are tabulated below:

| Agent | Vehicle | Blanching Score | | |
|---|---|---|---|---|
| | | 1 hr. | 5 hrs. | 24 hrs. |
| 1-phenyl-1-cyclo hexene (3%)** | 90% DMSO* | 1 | 0 | 0 |
| 4-phenylcyclo-hexanone (3%)** | 90% DMSO* | 1 | 0 | 0 |
| 2-hydroxy-4 methoxy-benzophenone | 90% DMSO* | 1 | 0+ | 0 |

*DMSO is the abbreviation for dimethyl sulfoxide, used in a ratio of 9:1, DMSO to water.
**Percents on a weight/weight basis of total composition (vehicle and agent).

These results indicate that post-irradiation application of a compound of the instant invention inhibits prostaglandin production as indicated by the reduction of inflammation evidenced by blanching.

The invention being thus described, it will be obvious that the same may be varied in many ways. Such variations are not to be regarded as a departure from the spirit and scope of the invention and all such modifications are intended to be included within the scope of the claims.

What is claimed is:

1. An anti-inflammatory composition comprising a therapeutically effective amount of an agent selected from the group consisting of 1-phenyl-1-cyclohexene, 4-phenyl-cyclohexanone and mixtures thereof in combination with a topically compatible, pharmaceutically acceptable carrier.

2. The composition of claim 1 wherein the agent is present in amounts of from about 0.05% to about 25% by weight of the composition.

3. The composition of claim 2 wherein the agent is present in amounts of from about 0.05% to about 15% by weight of the composition.

4. The composition of claim 3 wherein the agent is present in amounts of from about 0.1% to about 3% by weight of the composition.

5. The composition of claim 1 wherein the pharmaceutically acceptable carrier is selected from the group consisting of dimethyl sulfoxide; mono- and di-alcohols and polyols such as ethanol, 1-2-propylene glycol, polyethylene glycol, and glycerol; mineral oils; vegetable oils; petrolatum; nonionic, cationic and anionic surfactants; water; and mixtures thereof.

* * * * *